US008870944B2

(12) United States Patent
Sochman et al.

(10) Patent No.: US 8,870,944 B2
(45) Date of Patent: Oct. 28, 2014

(54) TWO VALVE CAVAL STENT FOR FUNCTIONAL REPLACEMENT OF INCOMPETENT TRICUSPID VALVE

(75) Inventors: Jan Sochman, Prague (CZ); Jan Peregrin, Prague (CZ)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/357,178

(22) Filed: Jan. 24, 2012

(65) Prior Publication Data

US 2012/0136430 A1    May 31, 2012

Related U.S. Application Data

(63) Continuation of application No. PCT/US2011/045255, filed on Jul. 25, 2011.

(60) Provisional application No. 61/370,362, filed on Aug. 3, 2010, provisional application No. 61/385,609, filed on Sep. 23, 2010.

(51) Int. Cl.
*A61F 2/06* (2013.01)
*A61F 2/82* (2013.01)
*A61F 2/24* (2006.01)

(52) U.S. Cl.
CPC ......... *A61F 2/2418* (2013.01); *A61F 2002/826* (2013.01); *A61F 2/2475* (2013.01); *A61F 2250/0008* (2013.01); *A61F 2250/0007* (2013.01); *A61F 2/2412* (2013.01); *A61F 2002/825* (2013.01)
USPC .......................................... 623/1.24; 623/1.3

(58) Field of Classification Search
USPC ...................... 623/1.24, 2.17, 1.26
See application file for complete search history.

(56) References Cited

U.S. PATENT DOCUMENTS

| 6,319,278 | B1 | 11/2001 | Quinn | |
|---|---|---|---|---|
| 7,070,616 | B2 * | 7/2006 | Majercak et al. | ............ 623/1.24 |
| 7,159,592 | B1 | 1/2007 | Makower et al. | |
| 7,530,995 | B2 | 5/2009 | Quijano et al. | |
| 2003/0014104 | A1 * | 1/2003 | Cribier | ......................... 623/2.11 |

FOREIGN PATENT DOCUMENTS

| EP | 1958597 A1 | 8/2008 |
|---|---|---|
| WO | WO 2009/092782 A1 | 7/2009 |
| WO | WO 2010/079426 A1 | 7/2010 |

* cited by examiner

*Primary Examiner* — Thomas J Sweet
*Assistant Examiner* — Tiffany Shipmon
(74) *Attorney, Agent, or Firm* — Woodard, Emhardt, Moriarty, McNett & Henry LLP

(57) ABSTRACT

A two valve caval stent for functional replacement of an incompetent tricuspid valve. The device is designed for minimally invasive percutaneous transcatheter placement and includes two stents connected by a bridge sized to span the right atrium, and two valves anchored by the stents in the superior and inferior vena cavas. Each of the valves optionally has a conical shape divided by supporting struts into three cusps that simulate the action of a native tricuspid valve.

14 Claims, 3 Drawing Sheets

TWO VALVE CAVAL STENT FOR FUNCTIONAL REPLACEMENT OF INCOMPETENT TRICUSPID VALVE

CROSS-REFERENCE TO RELATED APPLICATIONS

This application is a continuation of International Application No. PCT/US2011/045255, filed Jul. 25, 2011, pending, which claims the benefit of U.S. Provisional Patent Application Ser. No. 61/370,362 filed Aug. 3, 2010 and U.S. Provisional Patent Application Ser. No. 61/385,609 filed Sep. 23, 2010, all of which are hereby incorporated by reference in their entirety.

FIELD OF THE DISCLOSURE

This field of this disclosure concerns medical devices for implantation in the heart and, in particular, to a stent based valve device for replacement of an incompetent tricuspid valve.

BACKGROUND

An incompetent tricuspid valve causing tricuspid regurgitation (TR) occurs mainly from tricuspid annular dilation and right ventricular enlargement. TR is often secondary to left heart failure from myocardial or valvular causes, right ventricular volume or pressure overload and dilation of cardiac chambers. TR causes right atrial overload that is transmitted to the superior and inferior vena cava (SVC, IVC) and their tributaries. Eventually, this leads to hepatic congestion, ascites, peripheral edema and other clinical symptoms of congestive heart failure. Historically, tricuspid valve (TV) diseases have received less attention than diseases of the other heart valves. In the last decade, percutaneous transcatheter implantation of aortic and pulmonary valves has become an alternative to open heart surgery, particularly in high risk patients. However, TR did not receive attention of minimally invasive therapy until 2005 when Boudjemline et al developed a stent valve device and tested it in sheep to replace for their normal TV. Bai et al used a similar double-edge stent device for implantation into normal TVs in sheep. Both groups were successful in the majority of sheep tested, but expressed concern about device fixation, embolization, and the risk of myocardial trauma.

Placement of a self-expandable valve stent into the IVC between the hepatic vein origins and cavoatrial junction was first explored in normal swine by Como et al in 2003 as a potential treatment for failing total cavo-pulmonary connection. In a 2008 overview article on percutaneous replacement of heart valves, the same group mentioned placement of stent valves into the SVC and IVC for treatment of TR. Davidson & Cohn reviewing percutaneous valve repair in 2009 then referred to a case report of the use of stent-based valves in the SVC and IVC as functional replacement of TV. No procedure details and results were given and the case was referred as a case study presented at a Cleveland Clinic conference in 2006 by R. Greenberg.

The present invention is addressed to these and other concerns and improvements.

SUMMARY

The claims, and only the claims, define the invention. The following teachings and others that may be set forth herein or otherwise appreciated by those of ordinary skill in the art are achieved by the present disclosure. Among other things, there is shown and described a two valve caval stent for functional replacement of an incompetent tricuspid valve. In certain aspects, there may be provided a pair of vascular stents adapted for implantation in the superior and inferior vena cavas and a bridge connecting the stents. A pair of valves adapted to control blood flow through the superior and inferior vena cavas may be slidably disposed on the bridge so that the distance between the valves may be adjusted according to the anatomy of the patient. Fixation members may be attached to each of the valves allow the valve positions to be fixed along the bridge once the desired spacing is determined.

In a further aspect, the bridge may include a plurality of elongate connecting struts. In one form, there may be three connecting struts angularly spaced apart and upon which each of the valves is slidably disposed.

In a yet further aspect, the stents may be formed of a shape memory alloy and have a wire braided construction that permits self-expansion when deployed inside the superior and inferior caval veins.

Also, the valves may be formed as membranes having one or more leaflets or cusps, although alternative arrangements are also contemplated. The shape of the valves is preferably conical but may alternatively be flat, concave, convex, curved, or a combination of these shapes. Especially in the conical form, the valve membrane may be defined by three cusps in order to simulate the action of a native tricuspid valve in systole/diastole.

There is also disclosed methods of implanting the two valve caval stent into the superior and inferior vena cavas.

Other objects, embodiments, forms, features, advantages, aspects, and benefits shall become apparent from the detailed description and drawings included herein. An abstract of the technical disclosure in the detailed specification is provided for the purpose of complying with the rule in 37 CFR 1.72 but is not intended to be used for interpreting or otherwise limiting the scope of the claimed invention.

1A. Valves after adjustment fixed for ready placement in the superior and inferior vena cavas.

1B. Valves in neutral position prior to placement.

Figure 2:
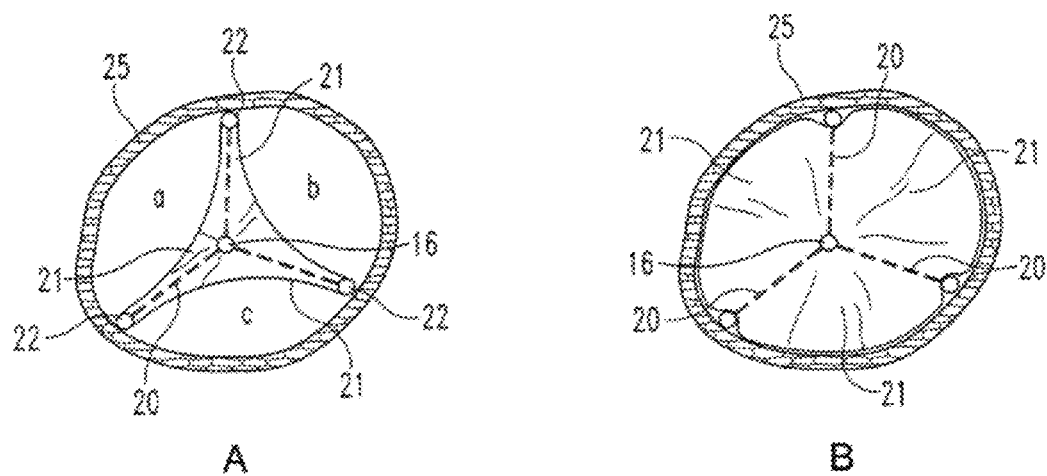

FIGS. 2A-B are schematic drawings depicting cross-sectional views of a caval vessel and illustrating the action of the three cusp cone shaped valve of the present invention in systole (2A) and diastole (2B).

FIGS. 3A-F show angiograms in a sheep with created tricuspid regurgitation treated with placement of the two valve caval stent (TVCS) of the present invention:

3A. Simultaneous bicaval angiogram shows diameters of central caval veins 20.1 mm and 22.1 mm, respectively. The distance between the intended sites of stent placement is 75 mm.

3B. Right ventriculogram shows a normal size right ventricle (RV) with early filling of the pulmonary artery (PA). No blood reflux in the right atrium is seen.

3C. Right ventriculogram after papillary muscle avulsion shows massive blood reflux into the right atrium (RA), superior vena cava (SVC) and inferior vena cava (IVC).

3D. Right ventriculogram immediately after the twin valve caval stent placement shows continued massive reflux into the RA and partial reflux into the SVC and IVC.

3E. Right atrial angiogram 1 hour after the TVCS placement demonstrates enlarged RV and RA and reflux to the caval veins to the TVCS valves. No reflux beyond the valves is seen.

3F. Simultaneous bicaval angiogram 3 hours after the twin valve caval stent placement shows good valve patency with filling of the RA and enlarged RV.

DETAILED DESCRIPTION

While the present invention may be embodied in many different forms, for the purpose of promoting an understanding of the principles of the present invention, reference will now be made to the examples, also sometimes referred to as embodiments, illustrated in the drawings and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As used in the claims and the specification, the following terms have the following defined meanings:

The term "bridge" means any structure providing a physical connection between two spaced apart structures and maintaining the space between them.

The term "caval" means of or relating to the vena cava of a body.

The term "cusp" means any fold or flap of a segmented valve, whether pointed, rounded, semi-lunar, part-lunar, or non-lunar in shape.

The term "stent" means a generally tubular and or polygonal structure having an opening therethrough and which is suitable for implantation with a body cavity such as the inferior and/or inferior vena cava to provide support and fixation within the body cavity and maintain the opening of the body cavity. The structure may be expandable, non-expandable and/or self-expanding, and may be formed of various metals, plastic and/or fabric materials. The structure may have a variety of open or closed wall constructions including but not limited to scaffolds, lattices, cages and/or wire meshes.

The term "valve" means a membrane structured to control flow through a body passage and limit backwards flow through the passage when the membrane is in a closed position. The membrane may be formed of various suitable biocompatible materials, including living and/or non-living tissues, and synthetic and/or natural fabrics.

Now referring to the specific illustrative embodiments shown in the drawings and described in detail herein, there is shown a two valve caval stent (TVCS) 10 of the present invention. Stent 10 was specifically sized for implantation in swine and sheep as part of our acute animal study that successfully evaluated its feasibility, but a similar design with modified dimensions may be suitable for use with humans. The two valve caval stent 10 generally comprises two caval stents 11 and 12 and associated valves 13 and 14 connected together by a connecting bridge 15 sized to span the right atrium.

Articles and phrases such as, "the", "a", "an", "at least one", and "a first", are not limited to mean only one, but rather are inclusive and open ended to also optionally include multiple such elements. Likewise, "comprising" is open ended and inclusive.

Figure 1:
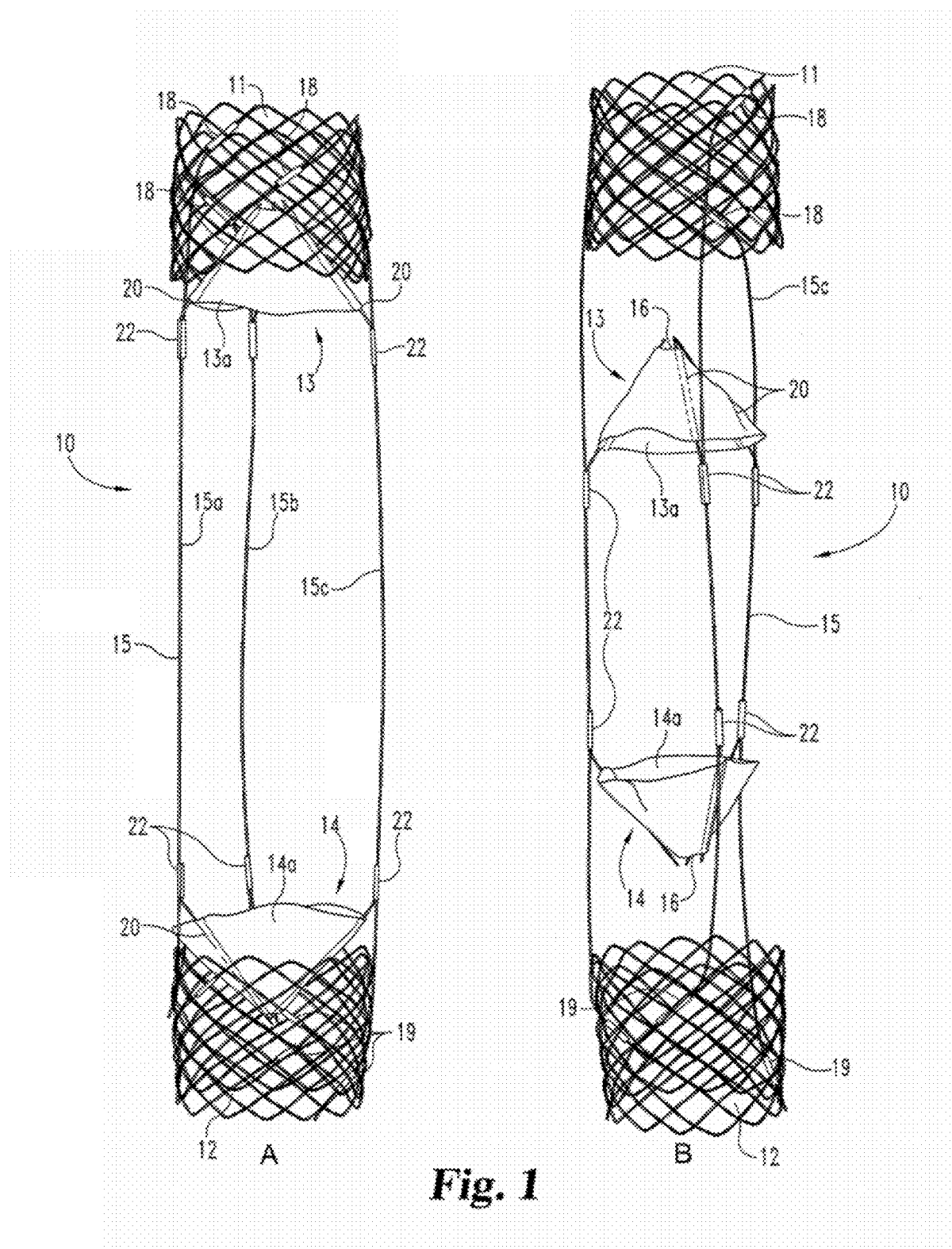
FIG. 1A-B is a top view of an illustrative embodiment of the two valve caval stent (TVCS). of the present invention showing.

The caval stents 11 and 12 are especially sized, designed and adapted for self-expanding implantation into the superior and inferior vena cavas, respectively, and thereby serve to anchor the position of associated valves 13 and 14. Caval stents 11 and 12 preferably are formed of a generally tubular shaped netting made from shape memory alloy nitinol 0.25 mm diameter wire formed in a cross-braided pattern. The tube diameter of the stents flares or increases from 21 mm at their peripheral ends to 25 mm at their respective centrally disposed ends, and their length in the expanded state (shown in FIG. 1) is about 25 mm. Each of the caval stents 11 and 12 also has an associated series of 3 barbs 18 and 19, respectively, mounted at their perimeters to prevent stent migration.

Although the stents 11 and 12 are preferably of the self-expanding type, it is also contemplated that other types of expanding stents, such as for example balloon expanding stents may also be used.

In a preferred arrangement, the stents 11 and 12 are SX model stents designed and manufactured by ELLA-CS, Hradec Kralove, Czech Republic. As the specific sizes described above and herein were intended for implantation in swine and sheep, some modification would of course be needed to accommodate the size and anatomical arrangement for each subject or patient, whether animal or human. In addition to size, other stent designs, materials and forms as are known in the art to be suitable for vascular implantation in the body may also be contemplated within the scope of the present invention.

Connecting bridge 15 connects the two caval stents 11 and 12 so as to form a unitary construction which allows both stents to be implanted in a single step, and which after implantation provides mutual support that serves to prevent any long-term migration of the caval stents from their desired implant positions in the superior and inferior vena cava, respectively. The phrase "long-term" as used herein is intended to refer to a period of years, as opposed to weeks or months, consistent with the anticipated remaining life expectancy of the subject. Connecting bridge 15 may have a variety of shapes and designs, but in the preferred exemplary embodiment is characterized by a series of three connecting struts 15a, 15b, and 15c, respectively. In a preferred form, the struts 15a-c are made from a shape memory alloy, e.g., nitinol, wire. Each of the struts 15a-c may optionally have a gold marker in its mid-portion for better orientation. The length of the connecting struts 15a-c is sized to space apart the stents 11 and 12 a sufficient distance to allow them to be positioned near the entrances of the superior and inferior vena cavas. This distance will vary depending upon the individual subject or patient, but in the swine/sheep feasibility study the lengths of the connecting struts 15a-c are sized so that the respective peripheral ends of the caval stents 11 and 12 are approximately 133 mm apart (FIG. 1A).

Reference will now be made to the specific construction of the valves 13 and 14. In the preferred embodiment shown, each of the valves 13 and 14 is formed of a flexible valve membrane 13a and 14a and has a generally conical or cone-shaped configuration. A small hole or aperture 16 approximately 1-2 mm in diameter is formed at the tip of the valve membranes 13a and 14a. The aperture 16 is sufficiently large to allow the slidable passage of a correspondingly sized guidewire but not large enough to allow an unacceptably large reflux blood flow when the valve are in their closed positions. In addition to allowing passage of a guidewire, the aperture 16 helps to minimize thrombus formation inside the cone-shaped membrane. The cone-shaped valves 13 and 14 are oppositely oriented so that they may be placed with their tips pointing against the direction of blood flow in both caval veins. The cone-shaped valves 13 and 14 are sized so that the maximum diameter of the valves in the full open position is approximately 2 mm larger than the superior vena cava and inferior vena cava ostia diameters.

Small diameter channels formed of the same material as the valve membranes 13a and 14a are spaced approximately 120 degrees apart and heat sealed onto the outer surface of the valve membranes. The channels receive three cone support struts 20 that delineate three segments or cusps 21 of the valve membranes 13a and 14a. These channels are only one of the possible options for valve membrane attachment to the cone support struts 20. Other options for this attachment could include sewing, gluing, welding, etc. according to the valve membrane material selection.

As may be appreciated with reference to FIGS. 2A-B, the configuration of the cone support struts 20 has an effect on the shape of the associated valve in its opened (i.e., systole) position. The cusps 21 flex inwardly and segment the blood flow in vessel 25 into three roughly equal spaces "a", "b", and "c" through the opened valve. The valve cusps 21 thus act somewhat like the three cusps of a native tricuspid valve in the body except that they have an inverse action in systole/diastole wherein the three cusps 21 move towards one another in the open valve position and away from one another to resume the cone shape configuration in the closed (i.e., diastole) position shown in FIG. 2B.

In the sheep/swine short-term designed study, the valve membranes 13a and 14a were made of 0.135 mm thin polyester membrane (Cathex Co, Ltd, Kanagawa, Japan) and were similar, although not identical, to the construction of the aortic valve disclosed in our paper by Sochman J., Peregrin J. H., entitled "A New Cone-Shaped Aortic Valve Prosthesis for Orthotopic Position: An Experimental Study in Swine" Cardiovasc Intervent Radiol 33:330-335 (2010).

Other suitable materials for the valve membranes 13a and 14a which may be suitable for long term implantation, especially in the human body, are also contemplated. For example, the use of small intestinal submucosa (SIS) covered with endothelial cells has been intensively studied for many long term uses in the body. In addition, endothelialization of bio-functionalised biomaterial is described by de Mel A, et al. in an article entitled "In situ endothelialization potential of a biofunctionalised nanocomposite biomaterial-based small diameter bypass graft". Biomed Mater Eng, 2009, 19(4-5): 317-331. Further possibilities include styrene-isobutylene-styrene (SIBS) produced by Innovia located in Miami, Fla., and biomaterials currently in use for percutaneous transcatheter or transapical catheter-based aortic valve implantation such as porcine and bovine pericardium harvested from animals.

As seen in FIGS. 1A-B, each of the cone-shaped valves 13 and 14, are mounted to the connecting struts 15a-c of bridge 15 with a series of 3 small stainless steel tubes 22 attached to the ends of cone support struts 20. These tubes 22 slide on the struts 15a-c before TVCS implantation and thereby enable the selection of proper valve positioning by allowing the valves 13 and 14 to slide towards or away from each other prior to fixation of the valves in their proper position by crimping the tubes on the connecting struts 15a-c with small pincers.

It may be understood that while the three cusp conical shape is preferred, the valves 13 and 14 may also assume a variety of other shapes and designs, including such other designs and constructions as would normally be considered suitable by those skilled in the art for long term use as a replacement for a native tricuspid valve. For example, other valve shapes and/or types also contemplated within the scope of the invention may include but not limited to bicuspid, flat, concave, convex, dome shaped, flutter, and other geometrically complex shapes.

The method of positioning the valves 13 and 14 within the SVC and IVC will now be described. The precise valve positioning depends upon the anatomy of the SVC and IVC and their entrances into the right atrium (RA), which may be visualized such as by simultaneous venography. The vertical length of the RA is used to determine the distance between the two cone-shaped valves 13 and 14. The desired spacing distance is slightly greater than the length of the right atrium. Once this distance is determined, small pincers are used to fix the valves 13 and 14 in their proper position along the struts 15a-c (FIG. 1B). The TVCS 10 is then backloaded into a 12 French size sheath and advanced with a pusher. When brought into the desired position, the TVCS 10 is implanted by pulling back the sheath while holding the pusher steady.

The principle of TVCS 10 action will now be described. With TV insufficiency, blood from the right ventricle (RV) returns during systole into the RA and flows into the SVC and IVC. The TVCS 10 prevents this retrograde blood flow and is intended to functionally replace the TV, but not in its orthotopic position. By blocking the entrances to the SVC and IVC during systole, the regurgitant blood from the right ventricle remains in the atrium and does not reflux into the organs that drain into the cava veins. In the upright position, the TVCS 10 protects the organs below the diaphragm, in reclined position the organs above the diaphragm. During ventricle diastole atrial pressure decreases and both cone-shaped valves 13 and 14 open to allow blood flow to the RA.

Swine/Sheep Feasibility Study

The swine/sheep feasibility study will now be described in detail. We conducted animal studies using an embodiment of the twin valve caval stent 10 of the present invention in one swine with a normal tricuspid valve without tricuspid regurgitation in order to evaluate its placement and also in three sheep with tricuspid regurgitation created by papillary muscle avulsion to evaluate its function. In two of the sheep, the twin valve caval stent 10 of the present invention was tested during fluid overload.

The test on the swine without TR was performed at the Experimental Research Laboratory of the Institute of Clinical and Experimental Medicine in Prague, Czech Republic.

Tests on the three sheep with TR were done at the Dotter Interventional Institute Research Laboratory in Portland, Oreg., USA. All experiments were conducted according to standard practices for handling laboratory animals. (Guide for the Care and Use of Laboratory Animals, U.S. National Institute of Health (NIH) Publication No. 85-23, rev. 1996) and were approved by the Institutional Animal Care and Use Committees of both institutions.

The animals weighed from 46 to 54 kg. The techniques used for their preparation and anesthesia were described in previous studies by Kim M D, Hoppe H, Pavcnik D, et al in their publication "Percutaneous Vein Occlusion with Small Intestinal Submucosa: An Experimental Pilot Study in Swine and Sheep" in Cardiovasc Intervent Radiol 30:725-730 (2007). The animals received heparin intravenously in doses of 5,000 units at the beginning of procedure and then 1,000 units one hour later. Respiration rate, expired carbon dioxide, oxygen saturation, EKG and pressures in the RV, RA, SVC and IVC were monitored during the procedures.

In the swine, where evaluation of TVCS placement was the study objective, a cut down was used for introduction of a 12 French size sheath into the right femoral vein. Two 5 French pigtail catheters, introduced into the left femoral vein and right jugular vein, were used for SVC and IVC venograms. After bicaval venography showed the distance between the central origins of the SVC and IVC was 63 mm., the TVCS valves 13 and 14 were then set to 2 cm longer than this distance. The device was back-loaded into a 12 French sheath and placed under fluoroscopic control using test injection of contrast material. The cephaled stent was placed into the SVC ostium and lower stent into the IVC ostium. TVCS 10 position and function was checked by fluoroscopy and repeated caval venograms for 3 hours. It functioned well for 3 hours without changing its position. No cardiac rhythm changes were observed. The animal was then euthanized and autopsy performed. Autopsy showed correct TVCS 10 position with no damage to the device structure. There was no disruption of RA, SVC or IVC.

Tricuspid regurgitation in the sheep was achieved by papillary muscle avulsion using a guidewire loop previously described by Hoppe H, Pavcnik D, Chuter T A, et al in their publication "Percutaneous Technique for Creation of Tricuspid Regurgitation in an Ovine Model" published in J Vasc Intery Radiol 18:133-136 (2007). The tip of a preshaped catheter with a thin guidewire was positioned under fluoroscopy under a papillary muscle from jugular vein approach. The guidewire was then caught by a goose-neck snare introduced from the other jugular vein. The guidewire loop was then pulled back, avulsing the papillary muscle. For the sheep induced with TR, percutaneous access was established in both jugular and femoral veins. A 12 French size sheath was placed into the right femoral vein for introduction of TVCS. A 10 French sheath placed into the left jugular vein was used for catheter avulsion of papillary muscle. Pigtail catheters (5 French) introduced into the right jugular vein and the left femoral vein were used for angiograms and pressure monitoring. Simultaneous SVC and IVC caval venograms (FIG. 3A) were done initially to document diameters of the SVC and IVC and distance between their central origins for TVCS selection. The simultaneous bicaval angiogram showed diameters of central caval veins 20.1 mm and 22.1 mm, respectively. The distance between the intended sites of stent placement is 75 mm. The TVCS valve diameters of 2 mm larger than SVC and IVC ostia diameters were selected. The distances between the valves were adjusted to 2 cm longer than the ostial distance. Baseline pressures were then measured and RV angiogram was done. After papillary muscle avulsion, pressure measurements and RV angiograms were repeated. The same studies were repeated again immediately and 1 hour and 3 hours after TVCS placement. RA angiograms were also done at 1 hour and 3 hours follow-ups. In 2 sheep, 3 liters of saline was injected intravenously in 30 minutes after the one-hour follow-up. After the 3-hour RV angiogram, simultaneous SVC and IVC venograms were done to document TVCS function and RV and RA sizes. The animals were then euthanized and autopsy was performed.

Figure 3:
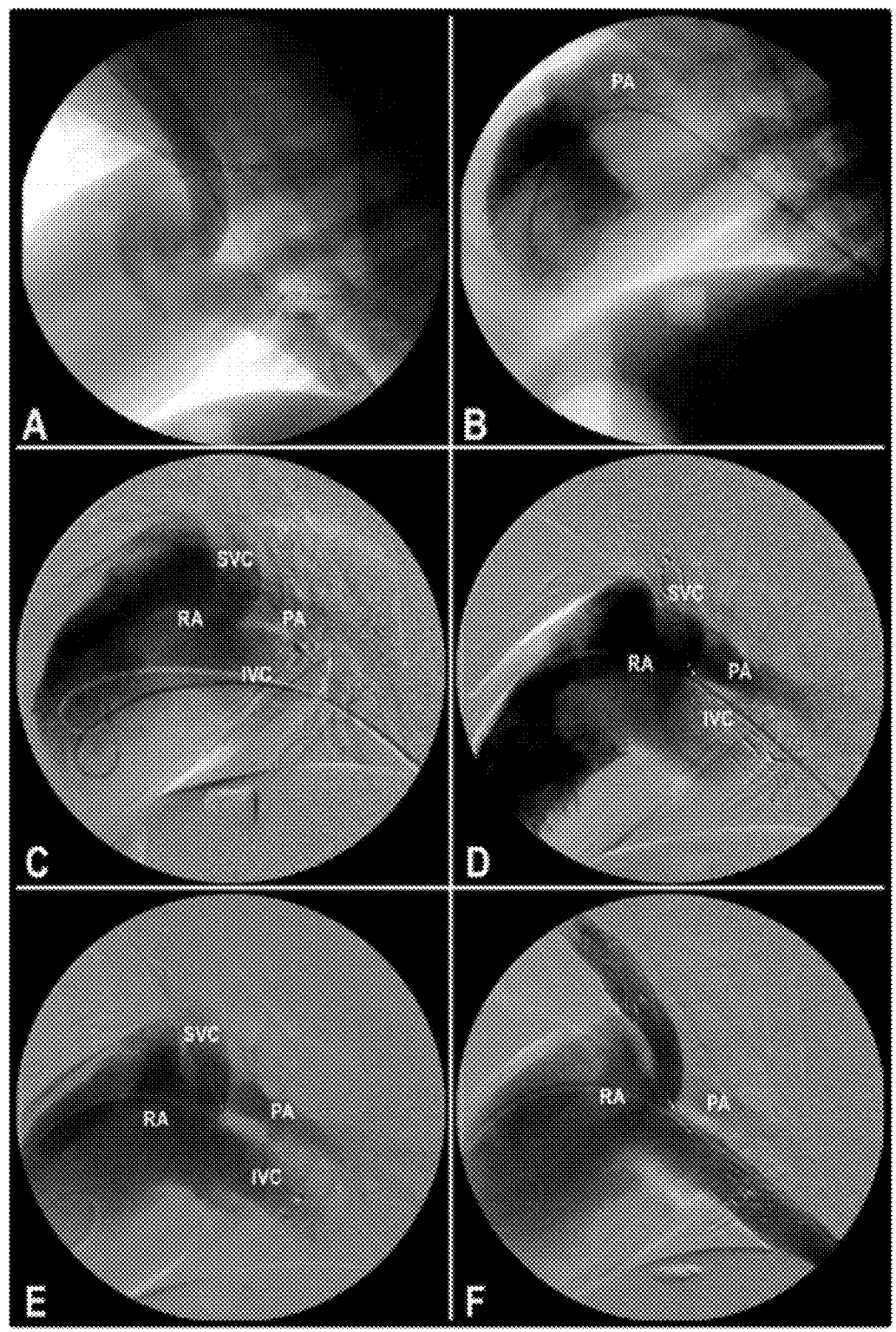

On bilateral caval venograms, the average ostial diameter of SVC in the 3 sheep with induced TR was 20.8 mm and that of IVC was 22.4 mm. Their average distance was 77.3 mm (FIG. 3A).

Table 1 below lists average pressures in the three sheep as measured in the right ventricle (RV), right atrium (RA), inferior vena cava (IVC), superior vena cava (SVC) before and after avulsion and the twin valve caval stent TVCS placement (Pressures are in mm Hg, the right ventricle pressure is systolic vs diastolic).

TABLE 1

| | RV | RA | IVC | SVC |
|---|---|---|---|---|
| Baseline | 23/5 | 6 | 5 | 6 |
| After avulsion | 24/6 | 7 | 8 | 7 |
| After TVCS | 26/13 | 8 | 8 | 8 |
| 1 hour later | 26/14 | 8 | 9 | 10 |
| 2 hours after fluid overload | 37/17 | 17 | 16 | 17 |

The average baseline pressures were: RV 23/5 mm Hg, RA 6 mm Hg, IVC 5 mm Hg and SVC 6 mm Hg (Table 1). The right ventriculograms showed well functioning ventricles with no reflux into the RAs (FIG. 3B). After papillary muscle avulsion, the pressures slightly increased (Table 1) and right ventriculograms documented significant TR with massive reflux of contrast medium into the RA and ostial portions of SVC and IVC (FIG. 3C). The TVCS 10 placement was followed by minimal increase of pressures in all measured sites that continued at 1 hour after placement (Table 1). In two animals with fluid overload, there were significant pressure increases in all sites measured (Table 1). Right ventriculogram after TVCS 10 placement demonstrated continued massive reflux into the RA and origins of IVC and SVC (FIG. 3D). Retrograde filling of IVC and SVC origins to the valves were well seen with RA angiogram. No reflux beyond the valves was seen (FIG. 3E). The 1-hour and 3-hour angiograms showed increasing enlargement of the RV and RA with minimal reflux into the caval vein origins. The 3-hour follow-up bilateral cavograms demonstrated good patency of the valves with filling of the enlarged RA and RV (FIG. 3F). In one sheep, there were no cardiac rhythm disturbances during the procedure. Atrial flutter developed in two other sheep after TR creation and ceased after TVCS placements. At autopsy, correct placement of the TVCSs and no damages of IVC, SVC or right atrium were found. The anterior papillary muscle was avulsed in all three sheep.

The studies we conducted of the TVCS 10 in 4 animals with 3 hours of follow-up gave promising results and showed that the TVCS 10 could be a potentially very useful device for functional replacement of incompetent TVs and alleviation of systemic effects of TR. The TVCS 10 can be easily introduced by back-loading and pushing through a 12 French sheath. This size is acceptable for the venous system in animals and can be easily adapted for humans. Depending on the size of the RA and distance between the central portions of the SVC and IVC, the distance of the two cone-shaped valves 13 and 14 can be optimized. The valves should extend about 1 to 2 cm into the SVC and IVC. The technique of TVCS 10 placement is basically the same as that of IVC filter placement. As a double stent device, the TVCS 10 can be easily and safely deployed in the selected positions under fluoroscopy using contrast injection tests. It does not spring forward during deployment after release from an introductory sheath as single body self-expandable stents sometimes do. The TVCS 10 also stays in a stable position, is not influenced by heart motion and does not embolize. We did not see any positional changes in our animals.

The TVCS 10 in 3 animals with TR functioned as intended. They eliminated blood reflux into the SVC and IVC, remaining functional during induced heart overload from infusion of a large amount of saline. While more investigation, particularly chronic studies, should ideally be done to fully evaluate TVCS 10 and prove its long-term efficacy in chronic alleviation of TR symptoms, the present studies support its usefulness. The long-term efficacy of TVCS 10 with TR should also be compared to that of animals receiving no treatment after TV avulsion. In this group of animals, close attention needs to be directed to changes in the right atrium since the overload state will be shifted to this chamber. Evaluation of chronic valve patency also should be an essential part of any such study to determine the material used to construct the valves 13 and 14 is sufficiently strong to maintain valve function and prevent clot formation over an extended period of time.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding.

While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

The invention claimed is:

1. A two valve caval stent for functional replacement of an incompetent tricuspid valve, comprising:
    caval valves including a superior vena cava valve and inferior vena cava valve, each of said caval valves including a flexible valve membrane having at least three cusps and a plurality of cone support struts supporting each of said cusps at angularly spaced apart locations, each of said flexible valve membranes having a generally conical shape allowing said cusps to flex inwardly and segment the blood flow through said valves;
    a first stent adapted to anchor said superior vena cava valve within the superior vena cava of a vertebrate body;
    a second stent adapted to anchor said inferior vena cava valve within the inferior vena cava of said body;
    a bridge, sized to span the right atrium, connecting said first and second vascular stents and said caval valves; and
    wherein the ends of said cone support struts opposite the apex of said conically shaped caval valves are non-cantilevered and are movably mounted to said bridge to adjust the distance between said caval valves prior to fixation inside the body.

2. The two valve caval stent of claim 1 wherein said bridge includes a plurality of elongate connecting struts having ends attached to said first and second stents.

3. The two valve caval stent of claim 2 wherein said bridge includes three or more of said connecting struts are angularly spaced apart.

4. The two valve caval stent of claim 1 wherein the length of said connecting struts is at least 10 centimeters.

5. The two valve caval stent of claim 1 wherein each of said caval valves is comprised of a flexible valve membrane having three cusps.

6. The two valve caval stent of claim 5 and further comprising:
    a plurality of support struts supporting each of said cusps of said caval valves at angularly spaced apart locations.

7. The two valve caval stent of claim 6 and further comprising:
    a plurality of mounting ferrules attached to each of said support struts and slidably mounted to said connecting struts, said mounting ferrules adapted to be crimped into a fixed position along said support struts so as to fix the position of said caval valves a pre-established spaced apart distance corresponding to the desired implant locations within the superior and inferior vena cavas.

8. The two valve caval stent of claim 7 wherein each of said flexible valve membranes has a generally conical shape and defines a tip aperture sized to allow slidable passage of a correspondingly sized guidewire.

9. The two valve caval stent of claim 1 wherein said first and second stents are formed of a cross-braided wire netting construction.

10. The two valve caval stent of claim 9 wherein said first and second stents are formed of a shape memory alloy and have a self-expanding construction.

11. The two valve caval stent of claim 10 wherein said first and second stents are generally tubular shaped and expand inside the body to a diameter varying from about 20 to 25 mm.

12. The two valve caval stent of claim 11 wherein said first and second stents have central facing and peripheral ends and a generally tubular shape that flares to an increased diameter at said peripheral end.

13. The two valve caval stent of claim 1 and further comprising:
    a plurality of barbs positioned along the periphery of said first and second stents.

14. The two valve caval stent of claim 1 wherein said bridge includes at least one orientation marker along its length.

* * * * *